(12) United States Patent
Takehara

(10) Patent No.: US 11,589,619 B2
(45) Date of Patent: Feb. 28, 2023

(54) ELECTROLYTIC GAS SUCTION TOOL

(71) Applicant: Aqua Bank CO.,LTD., Osaka (JP)

(72) Inventor: Takashi Takehara, Osaka (JP)

(73) Assignee: AQUA BANK CO., LTD., Osaka (JP)

( * ) Notice: Subject to any disclaimer, the term of this patent is extended or adjusted under 35 U.S.C. 154(b) by 583 days.

(21) Appl. No.: 16/603,782

(22) PCT Filed: Apr. 10, 2018

(86) PCT No.: PCT/JP2018/015005
§ 371 (c)(1),
(2) Date: Oct. 8, 2019

(87) PCT Pub. No.: WO2018/190322
PCT Pub. Date: Oct. 18, 2018

(65) Prior Publication Data
US 2020/0367571 A1    Nov. 26, 2020

(30) Foreign Application Priority Data
Apr. 12, 2017 (JP) .............................. JP2017-079322

(51) Int. Cl.
*A24F 40/46* (2020.01)
*C25B 1/04* (2021.01)
(Continued)

(52) U.S. Cl.
CPC ............ *A24F 40/46* (2020.01); *A24B 15/243* (2013.01); *A24F 40/05* (2020.01); *A24F 40/485* (2020.01); *A24F 40/50* (2020.01); *A24F 40/70* (2020.01); *A24F 40/90* (2020.01); *A61M 11/042* (2014.02); *B01J 23/42* (2013.01); *C25B 1/04* (2013.01); *C25B 9/65* (2021.01); *C25B 15/02* (2013.01); *C25B 15/08* (2013.01); *A24F 40/10* (2020.01); *A61M 2202/0233* (2013.01)

(58) Field of Classification Search
None
See application file for complete search history.

(56) References Cited

U.S. PATENT DOCUMENTS

2004/0107798 A1 *  6/2004  Hirata .................... B22F 9/082
                                                            75/331
2010/0263664 A1   10/2010  Radivojevic et al.
(Continued)

FOREIGN PATENT DOCUMENTS

CN      201499602 U     6/2010
JP      61-068061 A     4/1986
(Continued)

*Primary Examiner* — Harry D Wilkins, III
(74) *Attorney, Agent, or Firm* — Novick, Kim & Lee PLLC; Jae Youn Kim

(57) ABSTRACT

An electrolytic gas suction tool includes: a battery; a control substrate which controls power supply from the battery; a pair of positive and negative electrodes which are electrically conducted to or cut off from a positive electrode and a negative electrode of the battery by the control substrate; an electrolysis tank which is capable of storing water and into a lower part of which the pair of positive and negative electrodes are inserted in the mounted state; and a heater device which is heated to generate nicotine containing steam upon receiving the power supply from the battery by the control substrate.

7 Claims, 3 Drawing Sheets

(51) Int. Cl.
*C25B 15/02* (2021.01)
*C25B 15/08* (2006.01)
*A24F 40/485* (2020.01)
*A24F 40/05* (2020.01)
*A61M 11/04* (2006.01)
*A24F 40/70* (2020.01)
*A24F 40/90* (2020.01)
*A24B 15/24* (2006.01)
*B01J 23/42* (2006.01)
*C25B 9/65* (2021.01)
*A24F 40/50* (2020.01)
*A24F 40/10* (2020.01)

(56) References Cited

U.S. PATENT DOCUMENTS

| | | | | |
|---|---|---|---|---|
| 2014/0378745 A1* | 12/2014 | Lin | ............ | C25B 15/08 600/27 |
| 2015/0020823 A1 | 1/2015 | Lipowicz et al. | | |
| 2015/0144183 A1* | 5/2015 | Yang | ............ | H01L 31/0747 438/57 |
| 2015/0144482 A1* | 5/2015 | Lin | ............ | C25B 9/65 204/270 |
| 2015/0190604 A1* | 7/2015 | Lin | ............ | A61M 16/0833 128/202.26 |
| 2015/0282529 A1* | 10/2015 | Li | ............ | A61M 11/042 131/273 |
| 2016/0068972 A1* | 3/2016 | Lin | ............ | C25B 9/73 204/266 |
| 2016/0108528 A1* | 4/2016 | Lin | ............ | C25B 15/02 204/278 |
| 2016/0207765 A1* | 7/2016 | Takehara | ............ | C01B 3/065 |
| 2016/0263341 A1* | 9/2016 | Lin | ............ | C25B 9/17 |
| 2016/0263535 A1* | 9/2016 | Lin | ............ | B01F 23/23123 |
| 2018/0002822 A1* | 1/2018 | Lin | ............ | C25B 13/02 |
| 2018/0002824 A1* | 1/2018 | Lin | ............ | B01F 23/213 |
| 2018/0007966 A1* | 1/2018 | Li | ............ | A24F 40/42 |
| 2018/0028774 A1* | 2/2018 | Lin | ............ | C25B 1/04 |
| 2018/0056021 A1* | 3/2018 | Lin | ............ | C25B 15/00 |
| 2018/0057948 A1* | 3/2018 | Lin | ............ | A61M 16/125 |
| 2018/0209050 A1* | 7/2018 | Tak | ............ | C25B 11/075 |
| 2018/0223440 A1* | 8/2018 | Lin | ............ | C25B 1/04 |
| 2018/0228995 A1* | 8/2018 | Lin | ............ | C25B 15/08 |
| 2018/0250489 A1* | 9/2018 | Lin | ............ | A61M 16/12 |
| 2018/0251904 A1* | 9/2018 | Lin | ............ | C25B 15/08 |
| 2018/0320274 A1* | 11/2018 | Lin | ............ | C02F 1/4618 |
| 2018/0320275 A1* | 11/2018 | Lin | ............ | C25B 1/04 |
| 2019/0010618 A1* | 1/2019 | Lin | ............ | C25B 1/04 |
| 2020/0023155 A1* | 1/2020 | Takehara | ............ | C25B 15/02 |
| 2020/0138100 A1* | 5/2020 | Takehara | ............ | A24F 40/40 |
| 2020/0332424 A1* | 10/2020 | Takehara | ............ | C25B 9/17 |
| 2022/0143332 A1* | 5/2022 | Takehara | ............ | A61M 15/06 |

FOREIGN PATENT DOCUMENTS

| | | | | |
|---|---|---|---|---|
| JP | 2009-279241 A | | 12/2009 | |
| JP | 2010-531188 A | | 9/2010 | |
| JP | 2014-205874 A | | 10/2014 | |
| JP | 3193762 U | | 10/2014 | |
| JP | 2015-217116 A | | 12/2015 | |
| JP | 2017-12501 A | | 1/2017 | |
| JP | 2017-093755 A | * | 6/2017 | ............ A61M 16/00 |
| KR | 2009-0056246 A | * | 6/2009 | ............ A61H 9/0071 |
| KR | 10-2014-0128578 A | | 11/2014 | |
| WO | WO 89/11267 A1 | * | 11/1989 | ............ C25B 1/04 |

\* cited by examiner

ELECTROLYTIC GAS SUCTION TOOL

TECHNICAL FIELD

The present invention relates to an electrolytic gas suction tool which is portable and which allows a predetermined amount of hydrogen gas, oxygen gas, and nicotine-containing steam to be sucked in simultaneously or selectively.

BACKGROUND ART

A harmful effect of passive smoking due to sidestream smoke generated during smoking and due to exposure to tobacco smoke has become a social issue, and there has been provided a so-called electronic cigarette which emits no sidestream smoke containing tar, etc. or in which the amount of sidestream smoke, etc. is reduced. As the electronic cigarette, there exists a type in which a liquid containing nicotine is poured in and vaporized through heating or the like for suction, or a type in which a throwaway cartridge containing nicotine is connected and used each time smoking is performed. Further, in recent years, there has also appeared a so-called heating type electronic cigarette in which tobacco leaf is heated without being ignited so that solely the nicotine ingredient may be sucked in, with the sidestream smoke being prevented from being emitted (or being substantially reduced).

In the case of the conventional electronic cigarette, however, while it is possible to avoid the harmfulness to the health of passive smoking due to the sidestream smoke, etc., at least the smoker himself continues to take in nicotine. It is indispensable for him to reduce the nicotine intake amount of his own accord to quit smoking. After all, this does not help to quit smoking.

Conventionally, as the harmful effects of tobacco to the health, the following have been pointed out: (1) an increase in the risk of development of cancer due to the generation of active oxygen; and (2) an increase in the risk of motor disturbance or hardening of the arteries due to inhaling of carbon monoxide. Regarding item (1), active oxygen exhibits a very strong oxidizing force and serves to remove bacteria and viruses having entered the human body, whereas, as is known, it also attacks and damages normal human cells. Excessive intake of active oxygen increases the possibility of damaging normal cells, and leads to the risk of deterioration and mutation of the cells and skin aging. Typically, it increases the risk of developing cancer.

Regarding item (2), the intake of carbon monoxide, even in a small amount, leads to deterioration in the function of blood hemoglobin, and a slight oxygen shortage continues, which leads to deterioration in motor function and brain function. In some cases, the red blood cells increase to an abnormal degree, resulting, as pointed out, in high blood viscosity, an increase in blood pressure, and headache, leading sometimes to hardening of the arteries.

In this regard, in recent years, it has become apparent that hydrogen has a high function to remove active oxygen since hydrogen and active oxygen are combined to be reduced. Further, as is already known, the resultant substance of reaction between hydrogen and active oxygen is water, which is of very little negative influence on the human body. Thus, it is recommended that hydrogen be taken into the body during smoking, which is particularly likely to generate active oxygen in the body, which has been one of the causes in the diversion of the market of hydrogen water. Further, when combined with oxygen, carbon monoxide is turned into carbon dioxide to be detoxified, so that, during smoking, it is also recommended to taken in oxygen.

CITATION LIST

Patent Literature

Patent Literature 1: National Publication of International Patent Application No. 2017-500100
Patent Literature 2: National Publication of International Patent Application No. 2016-510970

SUMMARY OF INVENTION

Technical Problem

The present invention has been made in view of the aforementioned circumstances and has an object to provide an electrolytic gas suction tool which can simultaneously attain prevention of passive smoking and a reduction in the harm to the health of the smoker himself while allowing intake of nicotine and which can be freely carried about by the smoker.

Solution to Problem

In order to solve the aforementioned problem, a portable electrolytic gas suction tool of the present invention which makes it possible to suck in hydrogen, oxygen, and/or nicotine containing steam, includes:

a battery arranged in a battery receiving portion;
a control substrate which controls power supply from the battery;
a pair of positive and negative electrodes which are electrically conducted to or cut off from a positive electrode and a negative electrode of the battery by the control substrate;
an electrolysis tank which is capable of storing water, which is detachably mounted to the electrolytic gas suction tool, and into a lower part of which the pair of positive and negative electrodes are inserted in the mounted state;
a heater device which is heated to generate nicotine containing steam upon receiving the power supply from the battery by the control substrate; and
a mixing portion which mixes a gas flowing in from a channel fluidically connected to the negative electrode side of the pair of positive and negative electrodes in the electrolysis tank and a gas flowing in from a channel fluidically connected to the positive electrode side of the pair of positive and negative electrodes and to the heater device and guides a resultant mixture gas to a nozzle portion having a through hole.

In the above-described electrolytic gas suction tool, the heater device generating nicotine containing steam and the electrolysis tank electrolyzing water are controlled by the control substrate in the same device, and the gases emitted from them are mixed with each other in the mixing portion, and there is provided the channel guiding the mixture gas to a suction nozzle portion, so that it is possible to simultaneously take in nicotine, hydrogen, and oxygen. As described above, the harm to the health of nicotine intake can be mitigated through the intake of hydrogen and oxygen, and in the present electrolytic gas suction tool, it is possible to take in hydrogen and oxygen simultaneously with nicotine through the same smoking process. Further, the present electrolytic gas suction tool, in which all the members inclusive of the battery are arranged in the suction tool, is superior in portability, which advantageously makes it possible to perform suction easily at any place.

It should be noted, however, that hydrogen is reduced to water when oxidized, so that it is preferable not to pass it through heated air which is subject to oxidation and air of high oxygen concentration. In view of this, in the present electrolytic gas suction too, the channel leading from the negative electrode side where hydrogen is generated to the mixing portion is formed as a separate bypass channel. As a result, it is possible for hydrogen of high concentration to be directly taken in without being exposed to the heating by the heater device and the oxygen from the negative electrode.

Further, a partition member is provided in the electrolysis tank, the partition member passing between the pair of positive and negative electrodes and dividing the positive electrode side and the negative electrode side of the pair of positive and negative electrodes. It is preferable for the partition member to be fluidically connected on the lower side of the electrolysis tank.

As described above, in the case of incomplete combustion, nicotine and tar generate carbon monoxide, which is turned into carbon dioxide to be detoxified when oxidized. Thus, it is preferable for the oxygen emitted from the electrolysis tank to flow into the heater device generating nicotine containing steam (which also contains tar in some cases). In the present electrolytic gas suction tool, the positive electrode side generating oxygen and the negative electrode side generating hydrogen are divided from each other by the partition member, and the positive electrode side solely emitting oxygen and the heater device are connected to each other. Further, as described above, the negative electrode side is provided with the bypass channel leading to the mixing portion. As a result, it is possible to take in high-concentration hydrogen while detoxifying nicotine, etc. At the lower side of the partition member, there is a fluidic connection portion allowing ion exchange.

Further, it is preferable that the control substrate receives an electrical conduction signal to the pair of positive and negative electrodes based on an operation signal from the user and an electrical conduction signal to the heater device and performs power supply from the battery to the pair of positive and negative electrodes and to the heater device based on each signal, and it is preferable that the heater device is controlled such that the power form the battery is supplied to the heater device on condition that the power from the battery is being supplied to the pair of positive and negative electrodes.

In the present electrolytic gas suction tool, the operation of the heater device emitting nicotine is performed on condition that power is supplied to the positive and negative electrodes in the electrolysis tank to generate hydrogen and oxygen. Thus, unlike the case of the conventional electronic cigarette, the harm to the health due to nicotine intake is constantly reduced, and in the case where the amount of hydrogen and oxygen is large, the use of the present electrolytic gas suction tool is even good for the health.

Further, the control substrate may perform control so as to vary the power supply amount to the pair of positive and negative electrodes and the heater device in accordance with an operation signal from the user.

In the present electrolytic gas suction tool, it is also possible to gradually increase the intake amount of hydrogen and oxygen while reducing the nicotine amount, thus making it easier to effect conversion from the quitting of smoking to promotion of the health since by using the same device, the smoker is allowed natural transition from nicotine intake to the intake of hydrogen and oxygen.

More specifically, it is preferable that the channel fluidically connected to the negative electrode side of the pair of positive and negative electrodes in the electrolysis tank is directly connected to the mixing portion from an upper part on the negative electrode side divided by the partition member, and that the channel fluidically connected to the positive electrode side of the pair of positive and negative electrodes in the electrolysis tank and the heater device is connected to a lower part of the heater device from an upper part on the positive electrode side divided by the partition member and pass through the heater device to be connected to the mixing portion.

In an example, the mixing portion is attached to an upper part of the heater device and a bottom portion of the nozzle portion, the mixing portion is equipped with: a hydrogen gas channel fluidically connected to a through hole of the nozzle portion from the channel fluidically connected to the negative electrode side of the pair of positive and negative electrodes in the electrolysis tank; and an oxygen/nicotine-containing gas channel fluidically connected to the through hole of the nozzle portion from the channel fluidically connected to positive electrode side of the pair of positive and negative electrodes in the electrolysis tank and the heater device, and the hydrogen gas channel and the hydrogen/nicotine-containing gas channel join each other to be guided to the through hole of the nozzle portion.

In this electrolytic gas suction tool, there is provided one mixing portion which mixes the gases from the hydrogen bypass channel from the negative electrode side in the electrolysis tank and the channel for oxygen and nicotine having passed through the heater device from the positive electrode side in the electrolysis tank and which guides the mixture gas to the nozzle portion, thus providing a device of a small size, an integral shape and of high portability.

Further, in the present electrolytic gas suction tool, it is preferable that an oxygen gas transmission membrane is arranged between the upper part on the positive electrode side divided by the partition member and the lower part of the heater device.

An oxygen transmission membrane is provided between the positive electrode side emitting oxygen and the heater device. Due to the provision of the oxygen transmission membrane transmitting solely oxygen, it is possible to promote the oxidation of the carbon monoxide generated through incomplete combustion of nicotine, etc. Even in the case where the partition member is not provided, it may be possible to provide the bypass channel for hydrogen and oxygen up to the mixing portion (Although this structure has a demerit in that hydrogen is turned into water due to the oxygen contained, it helps to secure a predetermined amount or more of hydrogen since the state in which no heating is performed is maintained), and to provide an oxygen transmission membrane between the electrolysis tank and the heater device to oxidize the carbon monoxide.

Further, it is preferable that a platinum catalyst to be heated by the heater device is arranged in the heater device, and that the platinum catalyst is situated in the channel fluidically connected to the positive electrode side of the pair of positive and negative electrodes in the electrolysis tank and the heater device.

When a platinum catalyst is arranged in the heater device, and the platinum catalyst is heated simultaneously with the heating for generating nicotine, etc., carbon monoxide is oxidized by the platinum catalyst and the oxygen from the positive electrode side to be turned into carbon dioxide and detoxified.

Advantageous Effect of Invention

In the electrolytic gas suction tool of the present invention, it is possible to prevent passive smoking and, at the same time, mitigate the harm to the health of the smoker himself while taking in nicotine, and the smoker can freely carry about the suction tool.

DESCRIPTION OF EMBODIMENTS

Figure 1:
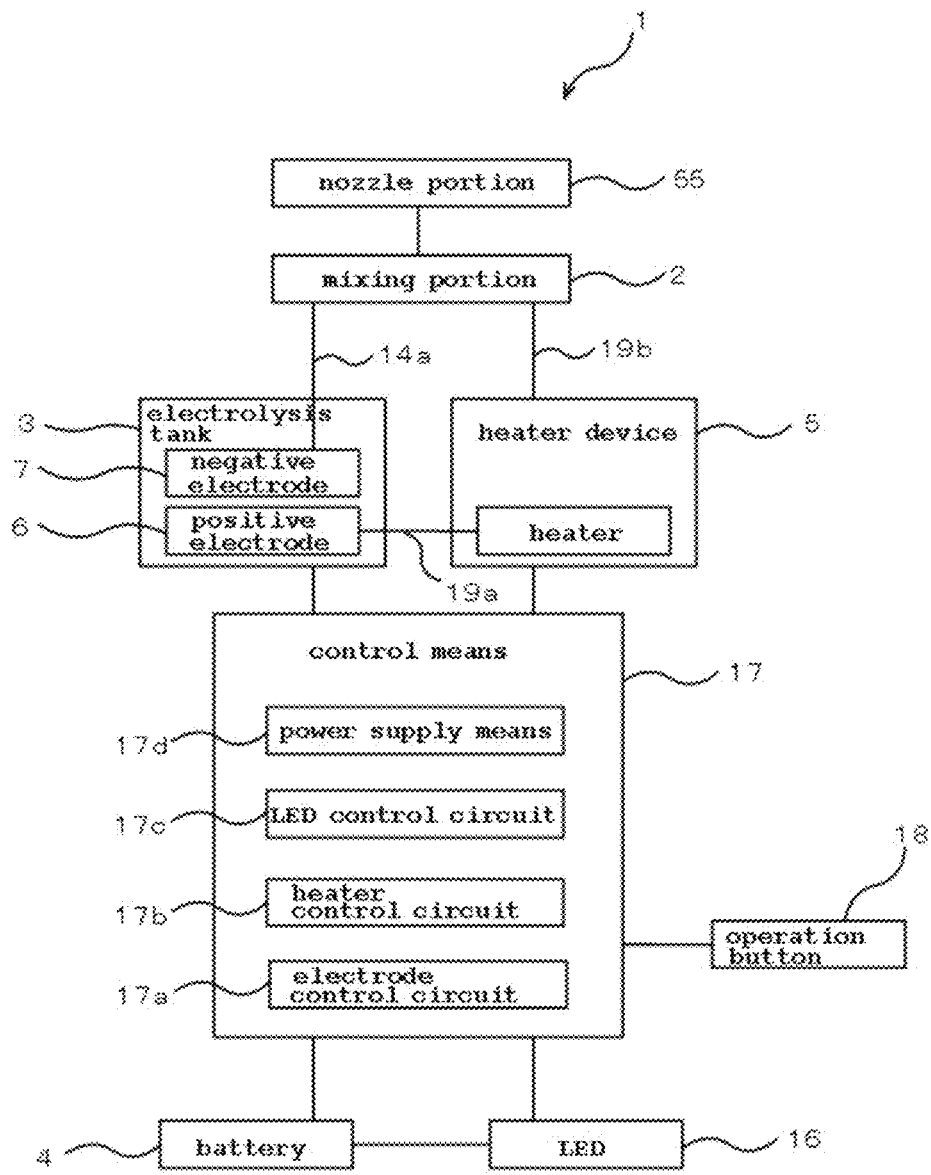
FIG. 1 is a schematic block diagram illustrating an electrolytic gas suction tool according to an embodiment of the present invention.
Figure 2:
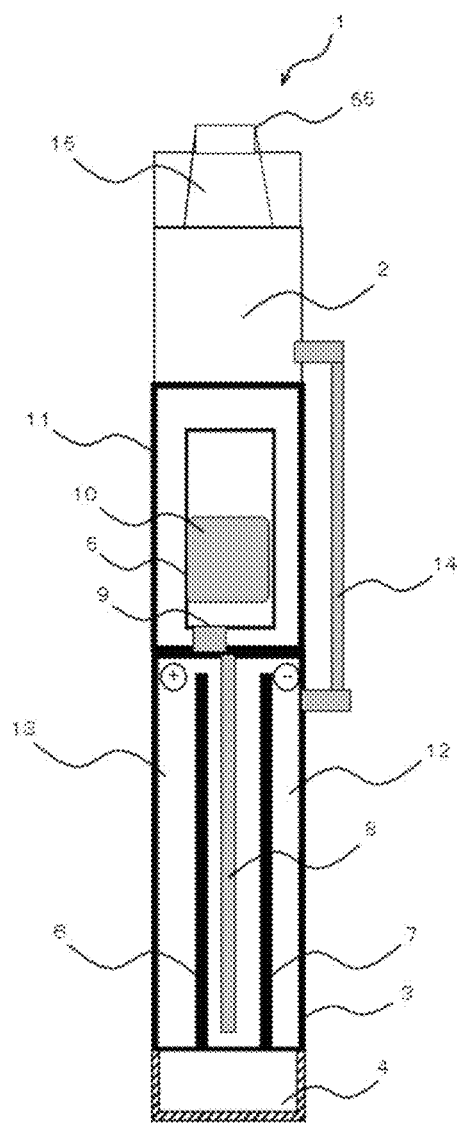
FIG. 2 is a schematic diagram illustrating an electrolytic gas suction tool according to an embodiment of the present invention.
Figure 3:
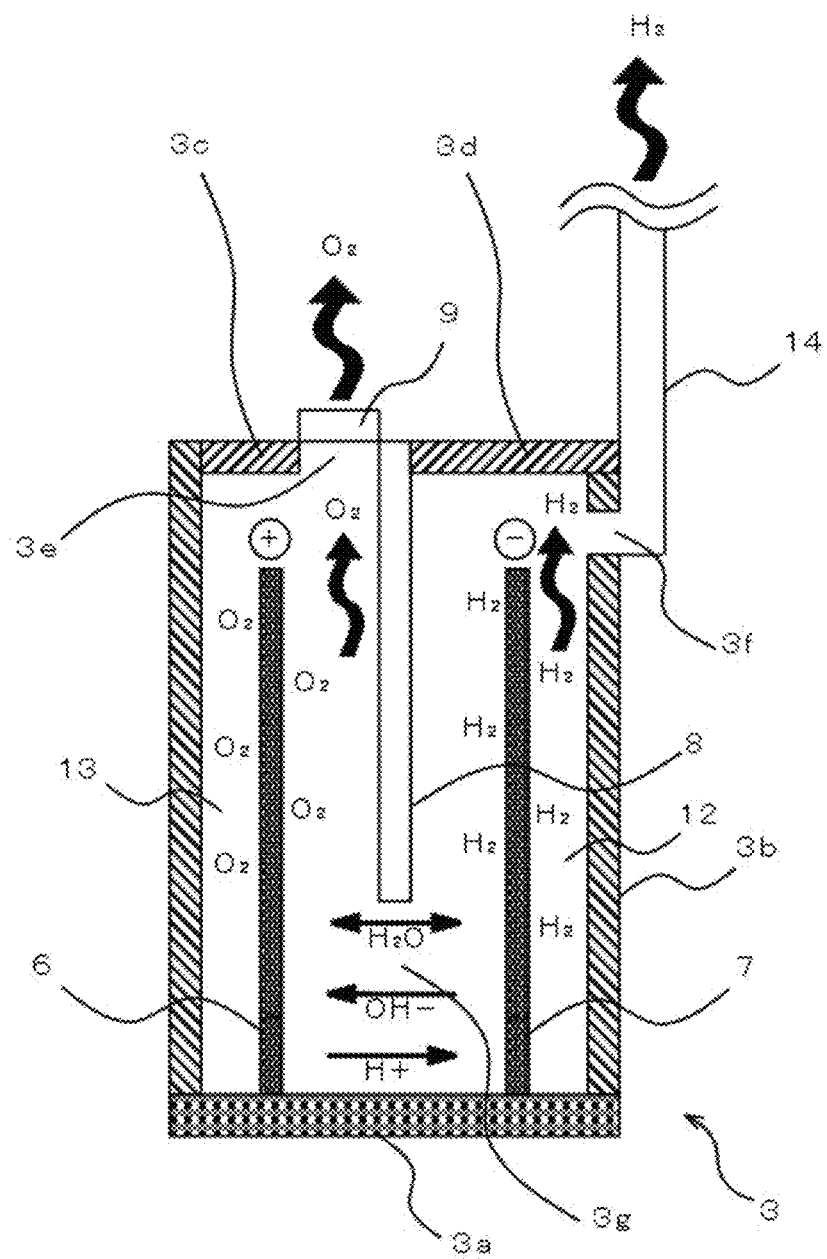
FIG. 3 is a schematic diagram illustrating how electrolysis is performed in an electrolysis tank of the electrolytic gas suction tool of the present invention.

In the following, an electrolytic gas suction tool according to an embodiment of the present invention will be described by way of example. FIG. 1 is a schematic block diagram illustrating an embodiment, FIG. 2 is a plan sectional view of a typical example of the embodiment of FIG. 1, and FIG. 3 is a schematic diagram illustrating how electrolysis is performed in the electrolysis tank of the electrolytic gas suction tool. The electrolytic gas suction tool of the present invention is not restricted to the one shown in the drawings. It goes without saying that the present invention also includes what is obtained through modification of what is shown and described without departing from the scope of common sense.

As shown in FIG. 1, the present electrolytic gas suction tool is generally composed of a battery 4, an LED 16, a control means 17, an electrolysis tank 3, a heater device 5, a mixer 2, and a nozzle portion 55. First, the battery 4 is a charging type battery, and a pair of positive and negative electrodes 6 and 7 are arranged in the electrolysis tank 3. Power from the battery 4 is supplied to the positive and negative electrodes 6 and 7 via a control means 33, and the LED 16 is connected to the battery 4. The control means 17 is equipped with an electrode control circuit 17a, a heater control circuit 17b, an LED control circuit 17c, and a power supply means (power supply circuit) 17d.

When the user operates an operation button 18, the electrode control circuit 17a controls the electrical conduction/interruption to the pair of electrodes 6 and 7 in the electrolysis tank 3 in response thereto, and the power amount from the battery 4 is varied by the power supply means 17d before being supplied to the electrodes 6 and 7. When power is supplied to the pair of electrodes 6 and 7, the water stored in the electrolysis tank 3 undergoes electrolysis. Oxygen is generated on the positive electrode 6 side, and hydrogen is generated on the negative electrode 7 side.

The hydrogen generated from the negative electrode 7 directly flows into the mixer 2 via a bypass channel 14. The oxygen generated from the positive electrode 6 temporarily flows into the heater device 5 via a channel 19a.

Solely in the case where it is determined by the electrode control circuit 17a that power supply (electrical conduction) is being effected to the pair of positive and negative electrodes 6 and 7 in the electrolysis tank 3, the heater device 5 controls the power supply to the heater in the heater device 5 in accordance with the operation of the operation button 18 by the user. Then, the heating temperature of the heater device is controlled through variation of the power amount supplied to the heater by the power supply means 17d. When power is supplied to the heater device 5, a steam containing nicotine, etc. is generated in the heater device 5.

The steam containing nicotine, etc. generated in the heater device 5 is mixed with the hydrogen having flowed in from the channel 19a before flowing into the mixer 2 via a channel 19b. Here, the heater device 5 heats a liquid, gel, or air sol containing nicotine, etc. by a heater to generate a steam containing nicotine, etc. Apart from this, it may also be possible to pour an aromatic oil or the like into the heater device 5 and to heat this, thereby generating a steam containing nicotine, etc. with aroma.

The hydrogen, the oxygen, and the steam containing nicotine, etc. from the bypass channel 14 and the channel 19b are mixed within the mixer 2 through joining of a hydrogen gas channel and an oxygen/nicotine-containing-steam channel (not shown) inside the mixer 2 that are respectively connected to the bypass channel 14 and the channel 19b before being connected to the nozzle portion 55. Then, the hydrogen, the oxygen, and the steam containing nicotine, etc. are sufficiently mixed with each other in the channel in the nozzle portion 55 before reaching the user suction port.

Next, a typical structure example of the electrolytic gas suction tool 1 of FIG. 1 will be described with reference to FIG. 2. As shown in FIG. 2, in the present electrolytic gas suction tool 1, an atomizer portion 11 in which the battery 4, the electrolysis tank 3, and the heater device 5 are arranged in that order as seen in FIG. 2, the mixer 2, a mouthpiece 15, and the nozzle portion 55 are connected to form a pipe-shaped whole. Or, in some cases, in order to form a pipe-shaped whole, the battery 4, the electrolysis tank 3, and the heater device 5 are inserted into a cover member (not shown) to be connected/arranged.

The battery 4 is of the charging type which is arranged inside a battery receiving portion (the outer surface of the battery 4 of FIG. 2 (the shaded portion). Inside the electrolysis tank 3, the pair of positive and negative electrodes 6 and 7 are erected so as to be opposite each other in the longitudinal direction. The lower ends of the pair of positive and negative electrodes 6 and 7 are respectively connected to the corresponding positive and negative electrodes of the battery 4 (The control means 17 shown in FIG. 1 is omitted here). Next, referring to FIG. 3, the structure of the interior of the electrolysis tank 3 and the way electrolysis is effected in the electrolysis tank 3 when the pair of positive and negative electrodes 6 and 7 are electrically conducted will be described.

As shown in FIG. 3, the electrolysis tank 3 storing water is generally composed of a tube member 3b which is hollow and which extends in the longitudinal direction, a bottom member 3a closing the bottom portion of the tube member 3b, and lid members 3c and 3d closing the upper part of the tube member 3a (The lid members 3c and 3d may be molded integrally). When the pair of positive and negative electrodes 6 and 7 are electrically conducted, oxygen ($O_2$) is generated in the vicinity of the positive electrode 6, and hydrogen ($H_2$) is generated in the vicinity of the negative electrode 7. The oxygen and hydrogen generated are of a lower specific gravity than water, so that they move upwards, each moving to a gap 3g. Here, the electrolysis tank 3 is provided with a partition member 8 extending downwards from the upper end of the tank and dividing the electrolysis tank 3 into a hydrogen gas generation layer 12 on the negative electrode 7 side and an oxygen gas generation layer 13 on the positive electrode 6 side. At the lower end of the partition member 8, there is provided a gap 3g extending from the upper surface of the bottom member 3a so as to fluidically connect the hydrogen gas generation layer 12 and the oxygen gas generation layer 13.

Due to this partition member 8, during the upward movement of the oxygen and hydrogen, mixing of the oxygen and hydrogen in the electrolysis tank 3 is hindered. On the other hand, at the lower part of the gap 3g provided at the lower part of the partition member 8 not divided by the partition member 8, free movement of water ($H_2O$), that is, movement of ions ($OH^-$ and $H^+$) required for generating oxygen and hydrogen, is possible. In this way, due to the partition member 8, mixing of oxygen and hydrogen is hindered while conducting electrolysis.

The lid member 3c closes the upper part of the oxygen gas generation layer 13. However, an opening 3e is provided at a portion of the lid member 3c or between the lid member 3c and the partition member 8 or the tube member 3b. The opening 3e is closed by a hydrogen transmission membrane 9. Thus, even if, due to the gap 3g, etc., hydrogen is leaked from the hydrogen gas generation layer 12 to the oxygen gas generation layer 13, the gas emitted to the exterior (into the heater device 5 in FIG. 2) by the oxygen transmission membrane 9 is restricted to oxygen.

Also in the hydrogen gas generation layer 12, the upper part of the hydrogen gas generation layer 12 is closed by the lid member 3d. However, an opening 3f is provided in the upper part of the tube member 3b on the hydrogen gas generation layer 12 side. The opening 3f is connected to the bypass channel 14. Thus, the hydrogen in the hydrogen gas generation layer 12 generated at the negative electrode 7 flows into the bypass channel 14, and flows upwards.

Referring again to FIG. 2, the mixer 2 is connected to the upper part of the atomizer portion 11 covering the heater device 5. The upper end of the bypass channel 14 is connected to the mixer 2, and hydrogen directly flows into the mixer 2. The oxygen having passed through the oxygen transmission membrane 9 flows into the heater device 5.

In the heater device 5, a mixture liquid such as nicotine oil is stored in the atomizer portion 11, and the mixture liquid is heated by the heater (not shown) to upwardly emit a steam containing nicotine, etc. The heater device 5 is provided with an oxidized platinum catalyst layer 10. When the platinum catalyst of this oxidized platinum catalyst layer 10 is heated by the heater device 5, the oxygen having flowed into the heater device 5 (or the atomizer portion 11) oxidizes the carbon monoxide into carbon dioxide through incomplete combustion of the nicotine, etc., thus detoxifying it.

The steam containing nicotine, etc. generated in the heater device 5 flows into a channel for oxygen and steam containing nicotine (not shown) in the mixer 2 connected to the upper part of the atomizer portion 11 (the upper part of the heater device 5). The lower part of the nozzle portion 55 is connected to the upper part of the mixer 2, and has in it a through hole (not shown) extending in the up-down direction. The hydrogen gas channel and the channel for oxygen and nicotine containing steam joining together within the mixer 2 are connected to the through hole of the nozzle portion 55, emitting the resultant mixture gas upwards (to the filter for the user) while mixing the hydrogen, the oxygen, and the steam containing nicotine, etc. through a predetermined approach section.

To protect the filter for the user, a mouthpiece 15 formed of a soft material such as resin may be connected to the upper part of the mixer 2.

The present invention is not restricted to the above-described embodiment of the gas suction tool but allows, as will be understood by those skilled in the art, modifications and improvements without departing from the scope of the claims and the gist of invention.

REFERENCE SIGNS LIST 1 electrolytic gas suction tool
2 mixer
3 3 electrolysis tank
3a bottom member
3b tube member
3c, 3d lid member
3e, 3f opening
3g gap
4 battery
5 heater device
6 positive electrode
7 negative electrode
8 partition member
9 oxygen transmission membrane
10 platinum catalyst (platinum oxide catalyst layer)
11 atomizer portion
12 hydrogen gas generation layer
13 oxygen gas generation layer
14 hydrogen bypass channel
15 mouthpiece
16 LED
17 Control means
17a electrode control circuit
17b heater control circuit
17c LED control circuit
17d power supply means
18 operation button (operation means)
19a channel
19b channel

The invention claimed is:

1. A portable electrolytic gas suction tool which makes it possible to suck in hydrogen, oxygen, and/or nicotine containing steam, comprising:
 a battery arranged in a battery receiving portion;
 a control substrate which controls power supply from the battery;
 a pair of positive and negative electrodes which are electrically conducted to or cut off from a positive electrode and a negative electrode of the battery by the control substrate;
 an electrolysis tank which is capable of storing water, which is detachably mounted to the electrolytic gas suction tool, and into a lower part of which the pair of positive and negative electrodes are inserted in the mounted state;
 a heater device which is heated to generate nicotine containing steam upon receiving the power supply from the battery by the control substrate; and
 a mixing portion which mixes a gas flowing in from a channel fluidically connected to the negative electrode side of the pair of positive and negative electrodes in the electrolysis tank and a gas flowing in from a channel fluidically connected to the positive electrode side of the pair of positive and negative electrodes and to the heater device and guides a resultant mixture gas to a nozzle portion having a through hole,
 wherein a partition member is provided in the electrolysis tank, the partition member passing between the pair of positive and negative electrodes and dividing the positive electrode side and the negative electrode side of the pair of positive and negative electrodes; and the partition member is fluidically connected on the lower side of the electrolysis tank.

2. The electrolytic gas suction tool according to claim 1, wherein the control substrate receives an electrical conduction signal to the pair of positive and negative electrodes based on an operation signal from the user and an electrical conduction signal to the heater device and performs power supply from the battery to the pair of positive and negative electrodes and to the heater device based on each signal; and the heater device is controlled such that the power from the battery is supplied to the heater device on condition that the power from the battery is being supplied to the pair of positive and negative electrodes.

3. The electrolytic gas suction tool according to claim 1, wherein the control substrate can perform control so as to vary the power supply amount to the pair of positive and negative electrodes and the heater device in accordance with an operation signal from the user.

4. The electrolytic gas suction tool according to claim 1, wherein the channel fluidically connected to the negative electrode side of the pair of positive and negative electrodes in the electrolysis tank is directly connected to the mixing portion from an upper part on the negative electrode side divided by the partition member; and the channel fluidically connected to the positive electrode side of the pair of positive and negative electrodes in the electrolysis tank and the heater device is connected to a lower part of the heater device from an upper part on the positive electrode side divided by the partition member and passes through the heater device to be connected to the mixing portion.

5. The electrolytic gas suction tool according to claim 1, wherein
the mixing portion is attached to an upper part of the heater device and a bottom portion of the nozzle portion,
the mixing portion is equipped with:
a hydrogen gas channel fluidically connected to a through hole of the nozzle portion from the channel fluidically connected to the negative electrode side of the pair of positive and negative electrodes in the electrolysis tank; and
an oxygen/nicotine-containing gas channel fluidically connected to the through hole of the nozzle portion from the channel fluidically connected to the positive side of the pair of positive and negative electrodes in the electrolysis tank and the heater device, and
the hydrogen gas channel and the oxygen/nicotine-containing gas channel join each other to be guided to the through hole of the nozzle portion.

6. The electrolytic gas suction tool according to claim 4, wherein an oxygen gas transmission membrane is arranged between the upper part on the positive electrode side divided by the partition member and the lower part of the heater device.

7. The electrolytic gas suction tool according to claim 1, wherein a platinum catalyst to be heated by the heater device is arranged in the heater device; and
the platinum catalyst is situated in the channel fluidically connected to the positive electrode side of the pair of positive and negative electrodes in the electrolysis tank and the heater device.

* * * * *